United States Patent [19]

Wallace et al.

[11] 4,115,543
[45] Sep. 19, 1978

[54] IDENTIFICATION OF *NEISSERIA GONORRHOEAE*

[75] Inventors: Rebecca Wallace, Ottawa; Fraser E. Ashton, Lucerne; Malcolm B. Perry; Benito B. Diena, both of Ottawa, all of Canada

[73] Assignee: Canadian Patents & Development Limited, Ottawa, Canada

[21] Appl. No.: 752,681

[22] Filed: Dec. 20, 1976

[51] Int. Cl.$^2$ .................... A61K 31/70; A61K 39/40; G01N 21/38; G01N 33/16
[52] U.S. Cl. ........................................ 424/8; 424/12; 424/85; 424/87; 424/92; 424/180; 536/1
[58] Field of Search .................... 424/8, 12, 13, 85, 87, 424/92, 93, 180; 536/1

[56] References Cited
U.S. PATENT DOCUMENTS 3,974,269  8/1976  Maley ..................................... 424/1.5

OTHER PUBLICATIONS

Perry, Can. J. Biochem., vol. 53, 1975, pp. 623–629.
Tramont, The J. Inf. Dis., vol. 130, 1974, pp. 240–247.
Maeland, Acta Path. Microbiol. Scand., vol. 73, 1968, pp. 413–422.
Danielsson, Applied Microbiol., vol. 27, Feb. 1974, pp. 368–374.
Menck, Acta Path. Microbiol. Scand., Sec. B, vol. 84, 1976, pp. 139–144.

*Primary Examiner*—Albert T. Meyers
*Assistant Examiner*—A. P. Fagelson
*Attorney, Agent, or Firm*—Alan A. Thomson

[57] ABSTRACT

A reagent and test for the identification of the bacterium *Neisseria gonorrhoeae*. Lipopolysaccharide antigen, found to be common to *N. gonorrhoeae* strains, is used to inoculate fowl, and serum from the fowl recovered containing antibodies causing agglutination of cells of all *N. gonorrhoeae* strains. The identification test comprises adding the recovered antibody reagent to a suspension of bacterial cells, the occurrence of cell agglutination being a positive test for *N. gonorrhoeae*.

10 Claims, No Drawings

IDENTIFICATION OF NEISSERIA GONORRHOEAE

FIELD OF THE INVENTION

A specific reagent and test for the identification of bacterial cells of *Neisseria gonorrhoeae* is described. A common gonococcal antigen (lipopolysaccharide) has been found and used to prepare antibodies by inoculating fowl and recovering antiserum from the fowl. The resulting antibodies have been found to be capable of causing agglutination of cells of any *N. gonorrhoeae*, this agglutination being made the basis of a rapid identification test.

DESCRIPTION OF THE PRIOR ART

The increased incidence of bacterial disease such as gonorrhea, which has now reached epidemic proportions, has focused on the need for rapid diagnostic techniques, in order to follow up contacts as quickly as possible. Presently, tests for the identification of *Neisseria gonorrhoeae* obtained from clinical specimens are beset with difficulties. Sugar fermentations frequently produce unsatisfactory growth patterns, require media of high quality and are time-consuming. A slide co-agglutination method has been described, using Protein-A containing staphylococci absorbed to the Fc portion of anti-gonococcal IgG (Danielsson, D., and Kronvall, G. Appl. Microbiol. 27:368-374). However, this method requires absorption of the gonococcal whole-cell antiserum with *Neisseria meningitidis*, and *Pseudomonas aeruginosa* or Morexella to render the reagent specific for *N. gonorrhoeae*. In addition, the co-agglutination test when used for the identification of *N. gonorrhoeae* in purity cultures grown on serum-containing medium was found to be inadequate, since 50% of the gonococcal strains tested gave pseudo-coagglutinations with the staphylococcal reagent (Menck. H. Acta path. microbiol. scand. Sect. B 84:139-144. 1976). A radioimmunoassay has been developed for detecting antibodies to *N. gonorrhoeae* in human serum (U.S. Pat. No. 3,974,269). This test which requires human blood samples and radioisotope measuring techniques is used to detect circulating antibody to *N. gonorrhoeae* but does not constitute a test for the actual identification of the causative microorganism, *N. gonorrhoeae*.

The fluorescent antibody (FA) test is sometimes used for the identification of *N. gonorrhoeae* in primary isolates from urogenital specimens. The reagent currently used for the FA test is derived from the rabbit. In specimens from other sites, namely throat, blood, joint exudate or cerebrospinal fluid, the FA test must be supplemented by sugar fermentation procedures. Considerable experience and costly equipment is required to use the FA test for the identification of *N. gonorrhoeae*.

Recently, M. B. Perry et al (Can. J. Biochem. 53:623-629, 1975) have found that a lipopolysaccharide isolated from *N. gonorrhoeae* colony type 4 is common to all strains of *N. gonorrhoeae*. This LPS is not immunogenic in rabbits, whether conjugated to a protein carrier or as such, while in mice an immunogenic effect was observed.

SUMMARY OF THE INVENTION

On further investigation, we have found that this common lipopolysaccharide has an active antigenic effect in fowl, e.g., hens, chickens, etc. causing the production of antibodies to *N. gonorrhoeae*. We have also found that these fowl antibodies are capable of agglutinating cells of all *N. gonorrhoeae* strains tested. The invention is thus directed to this preparation of fowl antibody product and to its use in a direct agglutination test for identifying *N. gonorrhoeae*.

The invention includes a method of preparing a reagent comprising specific fowl antibodies causing agglutination of cells of *Neisseria gonorrhoeae*. This includes (a) providing lipopolysaccharide antigen which is isolated from *N. gonorrhoeae* colony type 4 and is common to *N. gonorrhoeae*, (b) inoculating live fowl with this lipopolysaccharide antigen in amounts effective to raise antibodies in the fowl, and (c) recovering blood serum containing the antibodies from the inoculated fowl. As an identification test for *N. gonorrhoeae*, the invention includes the further steps of mixing the antibody reagent with a sample of bacterial cells to be identified, and observing whether cell agglutination occurs, the occurence of agglutination being a positive test for *N. gonorrhoeae*.

The invention also includes the novel reagent causing agglutination of cells of any strain of *N. gonorrhoeae* comprising antibodies derived from fowl inoculated with lipopolysaccharide antigen which is common to *N. gonorrhoeae*.

Both the common lipopolysaccharide antigen and the fowl host seem to be unique and critical in producing this type of antibody product able to agglutinate cells of all strains of *N. gonorrhoeae* yet not other closely related or confusingly similar species. We endeavored to use other gonococcal antigenic components to raise antisera having the same properties and were unsuccessful. Other animals were inoculated with the common antigen (rabbits, mice, goats and rats) but the sera recovered were unable to cause agglutination of all *N. gonorrhoeae* strains tested. Thus the combination of the common lipopolysaccharide antigen and the fowl host has resulted in a unique antibody product able to serve as the key reagent in a simple agglutination type identification test.

DETAILED DESCRIPTION AND PREFERRED EMBODIMENTS

The common gonococcal antigen can be prepared as described in the above Perry et al. 1975 publication. This antigen can be more fully described as follows. The lipid component (on hydrolysis, methanolysis and GLC analysis) contained about 38% dodecanoic acid, 25% 3-hydroxydodecanoic acid and 11% 3-hydroxytetradecanoic acid. The major component in the non-lipid portion was a core oligosaccharide of approximate molecular weight about 1570 and having the molar ratio composition as in Table 1.

TABLE 1

| Composition of *N. gonorrhoeae* LPS (T4) core oligosaccharide | |
|---|---|
| Component | Molar Ratio |
| 2-Amino-2-deoxy-D-glucose | 1.97 |
| D-Glucose | 2.00 |
| D-Galactose | 2.12 |
| L-glycero-D-manno-Heptose | 0.96 |
| 3-Deoxy-D-manno-octulosonic acid | 0.95 |
| Phosphate | 0.92 |

The overall composition of the lipopolysaccharide LPS is given in Table 2.

TABLE 2

| Composition analysis of *N. gonorrhoeae* (T4) LPS | |
|---|---|
| Component | Weight % |
| 2-Amino-2-deoxy-D-glucose | 13.8 |
| D-Glucose | 6.0 |
| D-Galactose | 6.9 |
| L-glycero-D-manno-Heptose | 3.8 |
| 3-Deoxy-D-manno-octulosonic acid | 7.3 |
| Phosphorus | 3.6 |
| Total lipid | 44.0 |
| Ethanolamine | Trace |
| Protein | 0.2 |

The lipopolysaccharide antigen can be suitably inoculated into hens as a solution in physiological saline. A suitable inoculation dose range is from about 500 μg to about 2.5 mg antigen/kg body weight. The inoculation may be repeated at weekly intervals to give increased antibody titers in the fowl. A preferred inoculation regime in hens and recovery of antiserum is as follows:

About 500 micrograms of gonococcal lipopolysaccharide antigen is injected once a week for three weeks. A further 2.5 milligrams is given two weeks after the third dose and the fowl bled one week later. The blood (clotted) is held at about 40° C until the serum separates. After separation, the serum is stored at a low temperature (4° C or −70° C).

While hens or chickens are the preferred host for inoculation, other fowl could also be used.

The fowl antibody product can if desired be recovered by fractionation procedures and stored as lyophilized powder. Before use, this recovered antibody would be dissolved in distilled water.

We have conducted stability studies on the antisera obtained from hens immunized with lipopolysaccharide. Serum aliquots lyophilized, or stored at −70° C, −20° C or at 4° C, retained their activity for the full course of our study (6 months).

The antibody can be coupled to a protein or cell to give a more observable agglutination or clumping effect. This coupling can be accomplished by reagents able to react with reactive sites of both the protein or cell and the antibody, these reagents being e.g., compounds having two or more of the following reactive groups: azo, sulfonic acid, fluoro groups combined with nitro groups, azide, imine, and reactive chloro groups. These reactive groups are capable of reacting with the primary amino, sulfhydryl (mercapto), and hydroxyl sites in the polymer chains of the antibody substances and of the protein or cell surfaces. A representative list of known coupling agents is: bis-diazobenzidine, bis-diazobenzidine disulfonic acid, diazotized arsanilic acid, tetraazo-p-phenylenediamine, difluorodinitrobenzene, various carbodiimides, toluene diisocyanate, cyanuric chloride, dichloro-S-triazine, and N-t-butyl-5-methylisoxazolium perchlorate.

If desired, the antibody can also be tagged with a fluorescent or chromophoric marker as is known in the art, and the agglutination and staining effect on the cells of *N. gonorrhoeae* observed by appropriate spectophotometric and microscopic techniques. Fluorescein isothiocyanate (FITC) has been found to be the most suitable labeling agent because of its excellent fluorescent characteristics including both brightness and color which make it stand out against a background.

The agglutination identification test is carried out by combining the unknown culture sample with a solution of the antibody reagent preferably in the presence of buffered saline (preferred pH 7.2). Agglutination can be read against a dark background with the naked eye or under magnification. Agglutination of *N. gonorrhoeae* will usually occur a few seconds after admixture of antibodies and gonococci (positive test).

The test can be performed with a single colony grown on primary isolation medium, whether or not it has been treated with oxidase reagent and is therefore non-viable. The colony can be picked up, e.g., with a loop under a stereoscopic microscope and admixed directly with the specific antiserum.

It has been found that some strains of other unrelated types of bacteria such as some Streptococci may give positive results in the test. For instance, in extensive tests, 26 out of 77 strains of Streptococci were postive. There is no problem, however, in distinguishing streptococcus from gonococcus by the oxidase test, colonial morphology and gram staining. Serogroup B Streptococci, often found in vaginal specimens, were negative in the test (except for subgroup B II).

The following Examples are illustrative. As a buffer, Sorensen's buffered saline pH 7.2 with 0.5% formalin (0.5 ml of 37% formaldehyde in 100 ml of buffer) was used.

EXAMPLE 1

Antibody Preparation

Five hundred micrograms of the lipopolysaccharide antigen (of the type found common to *N. gonorrhoeae*), in physiological saline was injected intravenously via the media wing vein to white Leghorn hens once a week for three weeks. A further 2.5 milligrams was given two weeks after the third dose and the hens were bled by heart puncture 1 week later. The clotted blood was held at 40° C for 4 hours until the serum separated off. This hen serum was stored at −70° until required as a test reagent.

EXAMPLE 2

Slide Test

Two separate drops of buffer were placed on a slide sectioned off with a grease pencil, and samples of the unknown culture were emulsified into the drops to obtain a smooth suspension. Then 1 drop of the hen antiserum of Example 1 (1:4 dilution in buffer) was mixed with the cell-buffer mixture with a loop; one drop of buffer was added to the control mixture and also mixed with a loop. The slide was rocked gently for a few seconds and agglutination was read with the naked eye against a dark background, or facilitated by using a magnifying lamp. Agglutination usually occurred a few seconds after admixture of serum and gonococci. The test has been performed with a single colony whether or not it had been treated with oxidase reagent and was therefore non-viable. The colony was picked up with a 5 mm diameter loop under a stereoscopic microscope and admixed directly into both the serum dilution and buffer drops. (Size of the drops was 0.017 ml).

Table 3 shows that cells of *N. gonorrhoeae* representing all of the four colony types were agglutinated by the antiserum. All of the secondary cultures (not colony typed) were identified as *N. gonorrhoeae* by the slide agglutination test. None of the heterologous Neisseria species was agglutinated by the lipopolysaccharide antiserum.

TABLE 3

Agglutination of *Neisseria gonorrhoeae* and reaction of other Neisseria species with hen lipopolysaccharide antiserum

| Neisseria species | NA/NT[a] |
|---|---|
| *Neisseria gonorrhoeae* | |
| Colony Type 1 | 7/7 |
| 2 | 3/3 |
| 3 | 3/3 |
| 4 | 7/7 |
| Secondary cultures | 1006/1006 |
| *Neisseria meningitidis*[b] | 0/149 |
| *Neisseria lactamica* | 0/7 |
| Non-pathogenic Neisseria[c] | 0/14 |

[a]Number of strains agglutinated/number tested
[b]Strains tested represent all known serotypes of *N. meningitidis*
[c]Represents all other known species of Neisseria Occasionally, when controls were rough or clumpy, the test was performed using as diluent a 1:1 mixture of buffer and glycerol, although with experience, clumps of rough bacteria were readily distinguishable from agglutinated cells. Irrespective of the medium on which the culture was received whether containing antibiotics, or blood components, serological identification of *N. gonorrhoeae* did not present any problem (contrary to the difficulties encountered in a co-agglutination test where about 50% of the gonococcal strains had to be transferred to media without blood components Mencka H. 1976. Acta path. microbiol. scand. B 84:139-144).

Bacterial species other than Neisseria were tested for their reactivity with hen gonococcal LPS antisera. Forty-six strains of *P. aeruginosa*, 7 strains of *Branhamella catarrhalis*, 13 Acinetobacter (including 5 strains of Morexella) and 6 Lactobacilli were not agglutinated by the antiserum. Some strains of Streptococci were agglutinated. However, this cross-reactivity with Streptococci does not pose a serious problem since there is no difficulty in distinguishing colonies of Streptococci from *N. gonorrhoeae* either visually or with the aid of the oxidase test or gram stain.

In the course of extensive tests, 241 *N. gonorrhoeae* strains received from a local venereal disease clinic and other local agencies were used for parallel studies involving direct slide agglutination of the primary isolates and of the secondary cultures. In addition 24 *N. meningitidis* specimens were also tested in parallel. Of the gonococcal specimens, 239 (99.2%) were identified in primary cultures (Table 4) showing an excellent correlation with the serological diagnosis of secondary cultures. This procedure enabled an identification of *N. gonorrhoeae* to be made directly from the primary isolation medium, without the 2-3 day delay generally required for the confirmation of *N. gonorrhoeae* by bacteriological methods. Specimens of *N. meningitidis* were not agglutinated by the antiserum.

During these tests, three persons each independently tested 350 strains of *N. gonorrhoeae* or *N. meningitidis* and the results were in complete agreement. This test method is rapid, does not depend upon purity plate isolation, and has the added advantage of savings in both the technician's time and cost of materials which are incurred during presently used laboratory methods to identify *N. gonorrhoeae*.

TABLE 4

Identification of *gonorrhoeae* in primary isolates and correlation with identification in corresponding purity cultures

| | | | Number Agglutated | | |
|---|---|---|---|---|---|
| Specimen | Source | Number Tested | Primary Isolates | Secondary Cultures | % Correlation |
| *N. GONORRHOEAE* | | | | | |
| | Rectum | 26 | 26 | 26 | 100 |
| | Urethra | 148 | 147 | 148 | 99.3 |
| | Cervix | 65 | 64 | 65 | 98.5 |
| | Pharynx | 2 | 2 | 2 | 100 |
| | TOTAL | 241 | 239 | 241 | 99.4 |
| *N. MENINGITIDIS* (Isolated from Pharynx) | | 24 | 0 | 0 | 100 |

We claim:

1. A method of preparing a reagent comprising antibodies causing agglutination of cells of *Neisseria gonorrhoeae* comprising
   (a) providing lipopolysaccharide antigen of the type which is common to *N. gonorrhoeae*, said antigen having the following composition: (weight %)

| | |
|---|---|
| 2-Amino-2-deoxy-D-glucose | 13.8 |
| D-Glucose | 6.0 |
| D-Galactose | 6.9 |
| L-glycero-D-manno-Heptose | 3.8 |
| 3-Deoxy-D-Manno-octulosonic acid | 7.3 |
| Phosphorus | 3.6 |
| Total lipid | 44.0 |
| Ethanolamine | Trace |
| Protein | 0.2 |

(b) inoculating live fowl with this lipopolysaccharide antigen in amounts effective to raise antibodies in the fowl, and
   (c) recovering blood serum containing the antibodies from the inoculated fowl.

2. The method of claim 1 wherein the fowl are domestic hens or chickens.

3. The method of claim 1 wherein the antibodies are recovered and purified from the serum.

4. The method of claim 1 wherein the antigen core oligosaccharide has essentially the composition in molar ratio:

| | |
|---|---|
| 2-Amino-2-deoxy-D-glucose | 1.97 |
| D-Glucose | 2.00 |
| D-Galactose | 2.12 |
| L-glycero-D-manno-Heptose | 0.96 |
| 3-Deoxy-D-manno-octulosonic acid | 0.95 |
| Phosphate | 0.92 |

5. A reagent causing specific agglutination of cells of *Neisseria gonorrhoeae* comprising antiserum or antibodies derived from the antiserum from fowl inoculated with lipopolysaccharide antigen of the type which is common to *N. gonorrhoeae* said antigen being as defined in claim 1.

6. The reagent of claim 5 in lyophilized form.

7. The reagent of claim 5 in antiserum form.

8. The reagent of claim 5 in a fluorescent tagged form.

9. The reagent of claim 5 diluted with buffered saline.

10. A method of testing the presence of bacterial cells of *Neisseria gonorrhoeae* comprising mixing the reagent of claim 5 with a sample of bacterial cells suspected of being *N. gonorrhoeae* and observing whether cell agglutination occurs, the occurrence of agglutination being a positive test for *N. gonorrhoeae* with the exception of interfering streptococci strains.

* * * * *